United States Patent
Cooper et al.

[11] 3,947,686
[45] Mar. 30, 1976

[54] GRAPHITE COMPOSITE X-RAY TRANSPARENT PATIENT SUPPORT

[75] Inventors: Adrianus A. G. Cooper; Phillip M. Leopold, both of Alliance, Ohio

[73] Assignee: The Babcock & Wilcox Co., New York, N.Y.

[22] Filed: Apr. 25, 1974

[21] Appl. No.: 464,079

[52] U.S. Cl. ............................. 250/439; 250/451
[51] Int. Cl.² ........................................... G03B 41/16
[58] Field of Search ............ 250/439, 444, 451, 456

[56] References Cited
UNITED STATES PATENTS

| | | | |
|---|---|---|---|
| 3,449,570 | 6/1969 | Kok | 250/439 |
| 3,897,345 | 7/1975 | Foster | 250/439 |

Primary Examiner—Davis L. Willis
Attorney, Agent, or Firm—J. M. Maguire; A. P. Cefalo

[57] ABSTRACT

A patient support of an X-ray unit fabricated from a generally radiolucent graphite fiber reinforced epoxy outer shell and an inner foam core.

7 Claims, 8 Drawing Figures

GRAPHITE COMPOSITE X-RAY TRANSPARENT PATIENT SUPPORT

FIELD OF THE INVENTION

The present invention relates to a fiber reinforced plastic stretcher, and, more particularly, to body support platforms fabricated from a plurality of layers of graphite reinforced epoxy adapted to use in X-ray systems as a radiolucent platform for body support during X-ray photography.

PRIOR ART

At the present time, the stage of medical development has widely incorporated the X-ray machine into the diagnosis and therapy regimes of medicine. High voltage radiation therapy units have found some success in the treatment of various cancers, while the common lower voltage units are generally used in the photography of bone fractures and some internal ailments. A cancer patient, moreover, may be submitted to the bombardment from both the diagnostic and the therapy units. In connection with a cancer patient, the diagnostic unit generally employs a patient support platform upon which the patient is placed during the X-ray photography. The X-rays pass through the patient and the body support platform to a film cassette located behind the support, photographing the site such as a tumor or the like. By fixing the patient's position relative to the support platform, accurate coordinates may be established to pinpoint the tumor site for subsequent treatment by the therapy unit tuned to the tumor coordinates.

It appears, however, that excessive exposure of the patient is to be prevented if harmful secondary ailments are to be avoided. In this respect, recent laws have significantly limited the maximum permissible X-ray attenuation of the diagnostic body support platform. This significant reduction in X-ray attenuation of the support platform significantly reduces the power required to penetrate the patient's body and the support which reduces the overall radiation imposed upon the patient.

In order to accurately locate the site for subsequent pinpoint treatment by the therapy unit, the diagnostic X-ray unit must have some freedom of movement to scan the patient's entire body. Therefore, it is generally found desirable to employ a patient supporting platform with a viewing area, the region in which the pictures are to be taken, which does not interfere with the path of the moving X-ray equipment. Generally, a cantilevered fixed end support with a free end viewing area offers this freedom from interference about the support.

It appears, however, that a cantilevered supported beam will deflect to an applied load according to the beam's stiffness characteristics. Since accurate coordinate determination of the tumor location is a purpose of the diagnostic unit, the diagnostic body support must exhibit the same resistance to deflection and permanent deformation as the therapy unit's support to ensure that physical treatment planning (tumor site location) conditions are maintained in rigid dimensional conformity with treatment conditions. In most cases, however, the therapy unit's support is generally deflection free, being fabricated from stiff materials without regard to the transparency of the body support.

It is clear that a diagnostic support of low X-ray attenuation and high stiffness characteristics is desirable to prevent overexposure of the patient and to accurately dimensionally locate the tumor site. Also, the desired contour of the support must not interfere with the path of the moving X-ray equipment.

SUMMARY OF THE INVENTION

In accordance with the present invention, a diagnostic X-ray body support platform is provided wherein a portion of the body support is fabricated from a plurality of radiolucent layers of high modulus of elasticity graphite fibers imbedded in epoxy and disposed about a foam core. The graphite fibers provide the balance between the present low X-ray attenuation standard and the general freedom from deflection condition. A diagnostic body support fabricated in this manner has exhibited an X-ray attenuation significantly lower than prior supports, within present attenuation standards and within the required rigid deflection response.

The invented body support is basically a sandwich beam of top and bottom shells, with sidewalls generally incorporated in the top and bottom shell, about a foam core. A portion of the shells are fabricated from a plurality of layers of graphite fiber reinforced epoxy layers oriented along the longitudinal axis of the body support, laid up in aluminum molds, vacuum bagged and oven cured. A portion of the fiber reinforced epoxy layers are fabricated from an unidirectional high modulus of elasticity graphite fiber, with the fibers in each layer oriented in the longitudinal direction parallel to each other. The longitudinal unidirectional graphite fiber layers provide the required low attenuation quality while the longitudinal axis orientation of the layers provides the general deflection rigidity. Since the foam core has a low shear modulus, the fiber epoxy composite side walls must provide the shear strength of the body support. In the preferred embodiment of this invention, the vertical side walls incorporated in the bottom shell are generally fabricated from a two directional fiber, Kevlar 49, matrix. In this manner longitudinal layers of two directional fiber epoxy composite are oriented in the longitudinal direction of the support, in like manner as the graphite layers, and, moreover, provide shear strength as well as deflection rigidity due to the two directional nature of the fibers in the layers. It is noted that the required shear stiffness would be provided by side walls having the graphite layers (of unidirectional fiber) positioned in an angular lay up pattern. The transition area, or joint, between the graphite fiber layers and the two directional fiber layers is made in multiple lap joints.

In the preferred embodiment of this invention, the vertical side walls of the top shell are fabricated from graphite fiber composite in like manner as the top shell.

In the preferred embodiment, the fixed, non viewing, end of the body support is fabricated from glass epoxy layers, limiting the use of the more expensive radiolucent graphite layers to the viewing area. Therefore, a transition region between the viewing area graphite layers and the fixed end glass layers is also made in multiple lap joints. Accordingly, the bottom shell transition area in which the two directional side walls are a part thereof, is made in multiple lap joints of three dissimilar materials in two directions, length and width.

A diagnostic body support fabricated in accordance with this invention exhibited substantially reduced X-ray attentuation and sufficient deflection rigidity to come within the present standards, not obtainable by current body supports.

Various other objects and advantages will become more apparent from a consideration of the following description.

DETAILED DESCRIPTION OF THE PREFERRED EMBODIMENT

Figure 1:
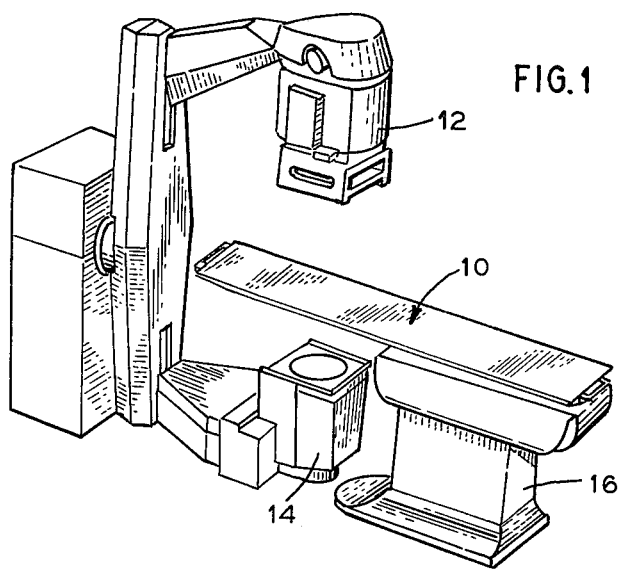
FIG. 1 is an isometric view of the diagnostic X-ray unit with a body support fabricated in accordance with the present invention.
Figure 2:
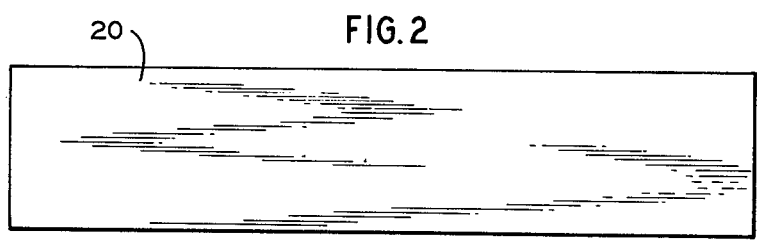
FIG. 2 is a plan view of the body support of FIG. 1.
Figure 3:
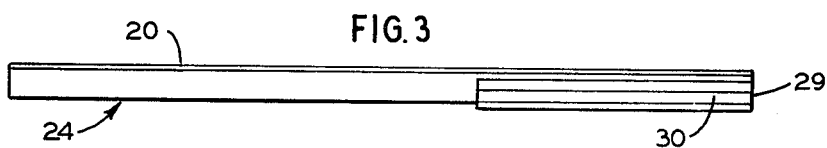
FIG. 3 is a side elevation view of a body support showing the fixed end attachment.
Figure 4:
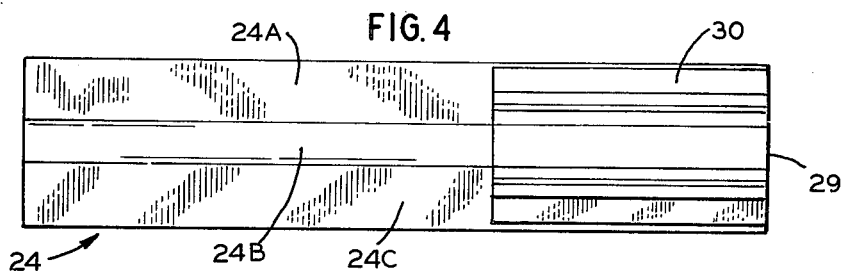
FIG. 4 is a bottom view of a body support and the apparatus for attaching the support to the X-ray unit.
Figure 5:
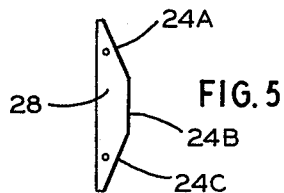
FIG. 5 is an end view of a support showing the external endplate.
Figure 6:
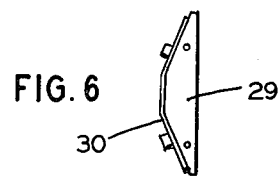
FIG. 6 is the other end view of a body support showing the fixed end attachement and end plate.

Attention is now directed to FIG. 1 of the drawings wherein a diagnostic patient body support platform generally designated 10 is shown in its functional position between the X-ray unit 12 and a film cassette 14. The body support platform is connected to a support stand 16 by any one of a number of conventional attaching means.

The patient body support platform 10, of this invention, is designed to meet the current X-ray attenuation, deflection stiffness and permanent deformation under load requirements not obtainable by present day patient body supports. Also, the body support's cantilevered contour does not interfere with the path of the moving X-ray equipment 12.

Shown in FIGS. 2 through 6 are the plan, elevation, bottom and side views of the preferred embodiment, in which the body support has a trapezoidal cross section contoured to the geometrical configuration compatable with the existing support stand 16. A portion of the body support comprises a top shell 20 and a bottom shell 24. The bottom shell 24 is trapezoidally shaped having a keel 24B and inclined side walls 24A and 24C. The body support's end portions are closed by the external end plates 28 and 29. Attached to bottom shell 24 and to end plate 29 is the fixed end attachment 30.

Figure 7:
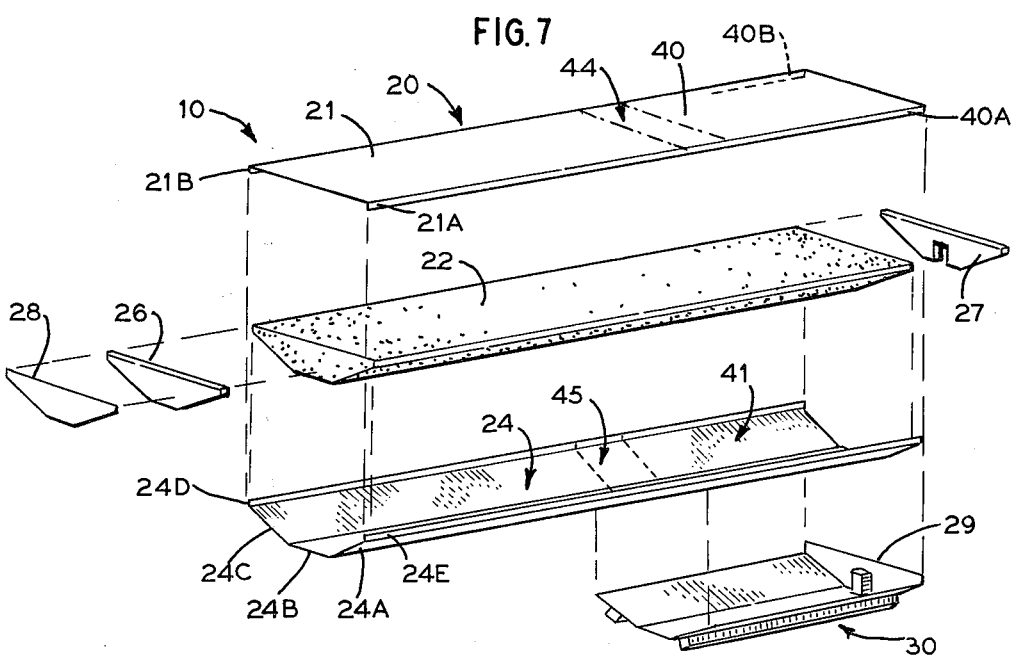
FIG. 7 is an exploded view of a body support.

Attention is now directed to FIG. 7 of the drawings wherein an exploded view of the preferred body support platform is illustrated. In general, the body support platform 10 is basically a sandwich beam having a top shell 20, an inner core 22, a bottom shell 24 and internal and external end closing means 26, 27, 28 and 29. A portion of the topshell 20 in general the viewing end 21 being fabricated from a plurality of layers of high modulus of elasticity about $30 \times 10^6$ psi, radiolucent unidirectional graphite fiber epoxy composite layers with the fibers oriented in the longitudinal direction of the layers and the layers oriented in the longitudinal direction of the support for deflection rigidity. The side walls 21A and 21B associated with the topshell viewing area 21 are also fabricated from a plurality of graphite fiber composite layers in like manner as the topshell viewing area 21. A typical topshell 21 of the type herein invented consists of 5 layers of graphite fiber epoxy composite, such as GY 70/Epoxy manufactured by Celanese.

The remainder of the topshell, in general the fixed non viewing end 40, is fabricated from a plurality of layers of glass fabric epoxy oriented in the longitudinal direction of the body support. Although not as radiolucent as the graphite layers, the glass layers, being confined to the non viewing area, do not interfere with the rays passing through the support platform. The side walls 40A and 40B are fabricated from a plurality of glass epoxy layers in like manner as the non viewing end 40.

In the topshell, the transition from the graphite to the glass is made in a 5 inch long multiple lap joint 44 in which the glass layers and the graphite layers are distributed such that warping due to differences in shrinkage and thermal expansion coefficients is minimal.

Returning to FIG. 7, the core 22 consists of generally radiolucent polyurethane foam. The foam core 22 affords substantial thickness to the sandwich structure, for deflection rigidity, while providing low overall and uniformity of X-ray absorption. The foam core 22, however, has a very low shear modulus, about 1800 psi, and shear strength must be provided for in the support's side walls. In the preferred embodiment the side walls associated with the bottom shell discussed below provide the required shear strength.

A portion of the bottom shell 24 is fabricated from a plurality of unidirectional graphite fiber epoxy composite layers with the graphite fibers oriented parallel to each other in the longitudinal direction of the layer associated therewith, and the plurality of graphite composite layers are oriented in the longitudinal direction of the support. In the preferred embodiment illustrated in FIGS. 2 through 7, the bottomshell 24, in general the keel 24B and a portion of the inclined side walls 24A and 24C in the viewing area are fabricated from a plurality of graphite composite layers in like manner in the viewing area 21 of the top shell 20. However, since the body support's shear strength must be provided in the side walls, the remainder of the bottomshell, in general the remainder of the inclined side walls 24A and 24C and the vertical side walls 24D and 24E are fabricated from a plurality of two directional fiber epoxy composite layers. A suitable radiolucent two directional fiber composite is Kevlar 49 as manufactured by Du Pont.

The two directional fiber epoxy layers are laid up in the side walls in the longitudinal direction of the body support in like manner as the graphite layers in the remainder of the bottom shell, and provide the necessary shear strength and deflection rigidity due to the two directional nature of the fibers therein.

Since, in general, fewer layers are needed in the side walls than in the keel, the transition between the graphite layers in the bottomshell 24 decreases gradually in number from a maximum in the keel to a number which will blend in with the two directional, Kevlar, layers. The transition between the graphite layers and the two directional fiber layers in the inclined side walls 24A and 24C is made in a multiple lap joint and is discussed below.

It is noted that the graphite layers, of unidirectional fibers, being positioned in an angular lay up pattern would also provide shear strength and deflection rigidity.

The remainder of the bottomshell, the fixed or non viewing end 41, is generally fabricated from a plurality of glass fabric epoxy, as in the topshell 40. Glass fabric epoxy in both the topshell 40 and the bottomshell 41 reduces production cost, although, it is noted that the more expensive graphite fibers could be used in place of the glass epoxy.

Figure 8:
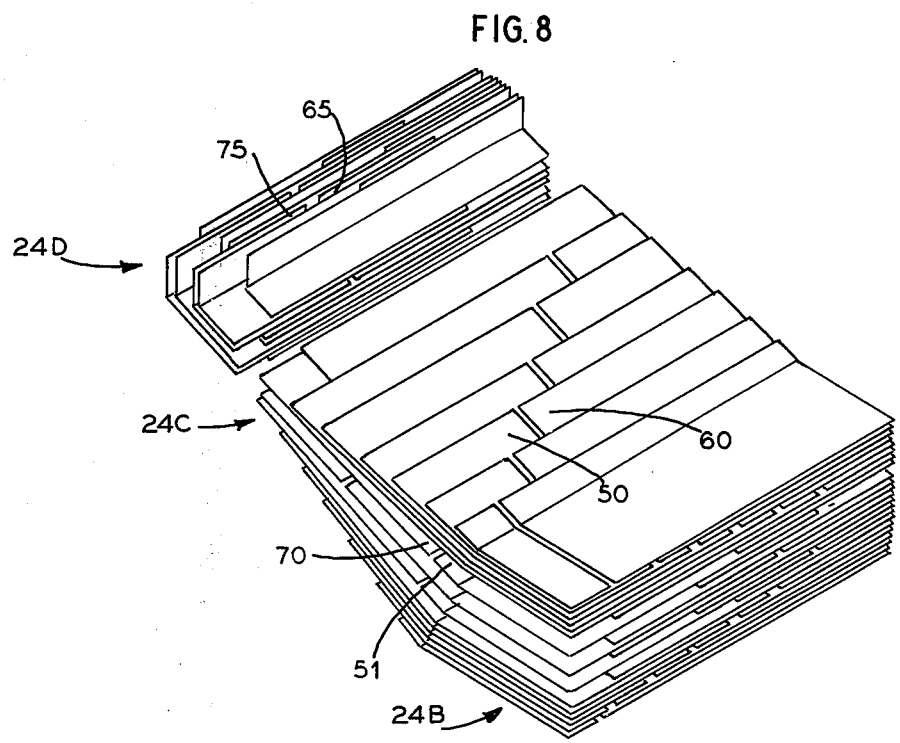
FIG. 8 is an isometric view of the transition overlap of the three dissimilar materials of a body support.

The glass epoxy portion 41, the graphite fiber of portion 24B and a portion of 24A and 24C and the two dimensional (Kevlar) fiber composite portion of 24A and 24C join in the bottom shell transition region 45 in two directions, length and width. FIG. 8 is a schematic representation of a section of the bottomshell transition region. The graphite layers 50 in the keel 24B and a portion of the inclined side walls 24A and 24C are lap joined in the length direction with glass layers 60. Also, some of the graphite layers 51 in a portion of the inclined side walls 24A and 24C similarly join in the width direction the Kevlar 49 fibers 70 in the remaining portion of the side walls. Simultaneously, the Kevlar 49 fibers 75 in the vertical side walls 24D and 24E are lapped joined with the glass fibers 65 in the length direction. These Kevlar-glass lapped joints are consistent with the graphite-Kevlar transition in the side walls 24A and 24C and with the decrease of the number of glass layers from the keel into the inclined side walls.

It will be appreciated that since the Kevlar, two directional fibers run in two direction in each layer, a layer of this fiber composite placed on the outside and inside of the top graphite shell and the multi-material bottom-shell will protect the outside surface from scratching and increase the shell integrity in the width direction.

In the trapezoidal shaped support of FIGS. 2 through 7, the bottom side wall shell 24 generally consists of 15 layers of unidirectional graphite fiber, oriented in the length direction, in the keel 24B, and 4 layers of Kevlar 49 fibers in the vertical walls and in a portion of the side walls. As viewed from the keel, the graphite layers decrease gradually in number and blend with the 4 Kevlar 49 layers, in the lap joining method of above, as illustrated in FIG. 8.

In the fabrication of the body support 10, the bottom-side wall 24 layers are longitudinally laid up in an aluminum mold, vacuum bagged and oven cured. The foam core 22 is then formed to fit the bottom-side wall shell and along with the internal end plates 26 and 27 it is bonded into the bottomside wall shell. The bonding agent or adhesive is an epoxy selected to have a low X-ray attenuation as well as the capability of being evenly distributed. Since uneven distribution is the largest contributor to localized variations in X-ray attenuation of the support, linen sheet is used in the bond to retain the adhesive and ensure even distribution thereof.

During bonding of the core 22 to the bottom-side wall shell 24, the bottom-side wall shell acts as a molding fixture while pressure is applied by vacuum bagging. Upon completion of the bonding operations, the core bottom shell unit is trimmed to accept the topshell. The topshell 20 generally being fabricated from graphite composite layers and glass epoxy layers is longitudinally laid up in an aluminum mold, vacuum bagged and cured. The cured topshell is bonded to the core bottomshell unit with pressure applied by vacuum bagging. Since the side walls provide the shear stiffness of the support, the width of the bond between the vertical side walls of the bottom shell and the top shell is allowed sufficient contact area to compensate for locally imperfect bonding during fabrication.

Returning to FIG. 7, the external endplate 28 and the external end plate 29 with the fixed end attachment 30 are bonded to the support's ends and bottomshell to complete the support structure.

The patient support fabricated in accordance with this invention obtained the following results with respect to X-ray attenuation and deflection stiffness.

TABLE I

| PROPERTY | REQUIREMENTS | RESULTS |
| --- | --- | --- |
| Attentuation (in viewing area) | equivalent to 1 mm Al or less | equivalent to .95 mm Al |
| Tip Deflection (300 lb. load) | 0.3" – 0.9" | 0.4" |
| Permanent Deflection (tip loaded to 600 lb.) | 0 | 0 |

The embodiments of the invention in which an exclusive property or privilege is claimed are defined as follows:

1. An X-ray machine system having an X-ray emitter, a film cassette and a patient support having a longitudinal axis and end portions disposed between the emitter and the film cassette wherein the patient support comprises, a supporting platform having a shell, a portion of said shell being fabricated from a plurality of layers of generally radiolucent unidirectional graphite fiber epoxy composite, each layer having a longitudinal axis, the graphite fibers in each layer being oriented parallel to the longitudinal axis of the layer and the composite layers being oriented parallel to the longitudinal axis of the support, an inner core fabricated from a generally radiolucent polyurethane foam, said inner core being joined to said composite layers by a generally radiolucent bonding epoxy, means for closing the end portions of said shell, and means for attaching the support to a stand.

2. A support as in claim 1 wherein a portion of the shell includes side walls fabricated from a plurality of two directional fiber composite layers.

3. A support as in claim 2 wherein a transition from the graphite fiber to the two directional fiber layers is arranged in a lap joint of multiple fiber layers.

4. A support as in claim 2 wherein a portion of the support is fabricated from a plurality of layers of glass fabric epoxy.

5. A support as in claim 4 wherein the transition from the glass fabric layers to the graphite and the two directional fiber layers is arranged in a lap joint of multiple fiber layers.

6. A support as in claim 1 wherein a linen sheet is employed in the bonding epoxy to contain and evenly distribute said bonding epoxy.

7. An article of manufacture comprising, an X-ray patient support having a longitudinal axis which includes, a supporting platform having a shell, a portion of said shell being fabricated from a plurality of layers of generally radiolucent unidirectional graphite fiber epoxy composite, each layer having a longitudinal axis, the graphite fibers in each layer being oriented parallel to the longitudinal axis of the layer and the composite layers being oriented parallel to the longitudinal axis of the support, an inner core fabricated from a generally radiolucent polyurethane form, and said inner core being joined to said composite layers by a generally radiolucent bonding epoxy.

\* \* \* \* \*